United States Patent [19]

Rideout

[11] 4,151,212
[45] Apr. 24, 1979

[54] PURIFICATION OF ETHYLENE DICHLORIDE

[75] Inventor: Walker H. Rideout, Corpus Christi, Tex.

[73] Assignee: PPG Industries, Inc., Pittsburgh, Pa.

[21] Appl. No.: 922,717

[22] Filed: Jul. 7, 1978

[51] Int. Cl.² ............................................. C07C 17/00
[52] U.S. Cl. .............................. 260/659 A; 260/652 P
[58] Field of Search ............ 260/659 A, 652 P, 662 A

[56] References Cited
U.S. PATENT DOCUMENTS 3,378,597  4/1963  Dehr et al. ............................ 260/652

Primary Examiner—Delbert E. Gantz
Assistant Examiner—Joseph A. Boska
Attorney, Agent, or Firm—Edward J. Whitfield

[57] ABSTRACT

The chloral content of ethylene dichloride, produced by the catalytic vapor phase oxychlorination of ethylene, is reduced by passing the gaseous effluent stream from the oxychlorination reactor through a bed of alumina.

5 Claims, No Drawings

PURIFICATION OF ETHYLENE DICHLORIDE

BACKGROUND OF THE INVENTION

Ethylene dichloride (1,2-dichloroethane) is typically produced by catalytic vapor phase oxychlorination of ethylene wherein a gaseous mixture of ethylene, hydrogen chloride, and oxygen are reacted in the presence of a Deacon-type catalyst, e.g., copper halide catalyst. The oxychlorination product gas stream is condensed to form organic and aqueous acidic liquid phases. The organic phase containing crude ethylene dichloride is further purified by, for example, distillation and the aqueous acidic phase is discharged to waste.

Although satisfactorily high yields of ethylene dichloride may be obtained by the vapor phase oxychlorination of ethylene, both the organic and aqueous phases typically contain objectionable amounts of chloral, i.e., from about 0.2 to 0.5 percent by weight, in the organic phase and in excess of 2 percent by weight in the aqueous phase.

Since chloral is classified as a pollutant, it must be substantially removed from the aqueous phase prior to discharge to waste and also must be removed from the organic phase in order to produce high purity ethylene dichloride.

One means of removing chloral from the condensed oxychlorination product stream is disclosed in U.S. Pat. No. 3,378,597 wherein aqueous sodium hydroxide is used to decompose chloral to chloroform and sodium formate. However, both chloroform and sodium formate also pose a waste disposal problem and require additional treatment, e.g., bioxidation or the like, before being discharged to a receiving stream.

It is desirable, therefore, to devise means for removing chloral prior to condensing the gaseous oxychlorination product stream which would preclude further treatment of both the organic and aqueous phases to remove chloral therefrom.

SUMMARY OF THE INVENTION

Chloral is removed from the product gaseous stream produced by catalytic vapor phase oxychlorination of ethylene by passing the product gas stream through a bed of alumina.

DESCRIPTION OF THE INVENTION

In accordance with this invention, it has been found that alumina is particularly effective in removing chloral from the product gas stream produced by the catalytic vapor phase oxychlorination of ethylene.

The alumina is in the form of a fixed or static bed and has a BET surface area of from about 30 to 600 square meters per gram, preferably from about 100 to 300 square meters per gram. The quantity of alumina is related to the volume of oxychlorination catalyst. Typically sufficient alumina is used to provide a volume ratio of alumina to oxychlorination catalyst of from about 0.1 to about 0.6, preferably from about 0.1 to about 0.3. A higher relative volume of alumina to oxychlorination catalyst is used when the alumina has a low BET surface area and conversely a lower relative volume of alumina to oxychlorination catalyst is used when the alumina has a high BET surface area.

Care should be taken that neither too much nor too little alumina be used. The use of too much alumina will result in an overly long contact time with the oxychlorination product stream which tends to decompose not only chloral but also ethylene dichloride product. Conversely with the use of too little alumina there will be insufficient contact time with the oxychlorination product stream resulting in incomplete decomposition of chloral.

The optimum volume ratio of alumina having a particular BET surface area to oxychlorination catalyst for a given system may, however, be readily determined without excessive experimentation simply by varying the volume of alumina to oxychlorination catalyst within the above specified limits bearing in mind that the higher the BET surface area of the alumina, the lower the relative volume of alumina based on the volume of oxychlorination catalyst.

The temperature of the alumina bed is maintained at from about 200° C. to about 300° C., preferably from about 240° C. to about 260° C., and, in order to obtain satisfactory decomposition of chloral, the oxychlorination product stream should contain from about 1 to 5 percent by volume oxygen.

In a typical practice of the invention, ethylene, hydrogen chloride, and oxygen gases are fed in known fashion to a fluid reactor containing an oxychlorination catalyst at a rate sufficient to maintain the catalyst bed in a fluidized condition without significant entrainment of catalyst particles in the product gas stream and to intimately contact the gaseous reactants with the fluidized catalyst. Of course, the vapor phase oxychlorination of ethylene to ethylene dichloride may be conducted using a fixed or static catalyst bed rather than a fluidized catalyst. Particle size of the oxychlorination catalyst is not particularly critical, although for fluid bed operation catalyst particle size is typically in the range of 30 to 200 mesh (U.S. Sieve), preferably between 40 and 100 mesh. The reaction may be conducted over a wide range of temperature, for example, between 150° C. to 500° C., preferably between 250° C. and 350° C. Contact time between the gaseous reactants is typically not more than about 30 seconds and usually about 10 seconds. Depending on reaction conditions and catalyst selection, conversion of ethylene to ethylene dichloride usually ranges from about 70 percent to substantially quantitative and ethylene dichloride crude having an ethylene dichloride content of from 97 percent to 99 percent may be obtained.

The product gas stream from the oxychlorination reactor is passed through a secondary reactor containing a fixed or static bed of particulate alumina maintained at a temperature of from about 200° C. to about 300° C., the volume of alumina being proportioned to the volume of oxychlorination catalyst in the fluid reactor as described hereinabove.

It is, of course, to be understood that rather than employing a single alumina containing reactor, two or more such reactors connected in series may be employed The gaseous stream, after passage through the alumina bed, is condensed in known fashion to form organic and aqueous liquid phases. The organic phase containing ethylene dichloride having a reduced chloral content is further purified by, for example, distillation, and the aqueous phase also having a reduced chloral content may be discharged to waste treatment to neutralize hydrochloric acid or depending on the hydrochloric acid content, the same may be recovered, if economical.

The effectiveness of alumina in removing chloral from a gaseous product stream produced by catalytic oxychlorination of ethylene is illustrated but is not intended to be limited by the following example.

EXAMPLE 1

Preparation of Oxychlorination Catalyst

About 2,233 grams of 30×60 mesh (U.S. Sieve) attapulgite clay were thoroughly mixed with about 2,250 milliliters of an aqueous solution containing about 645 grams cupric chloride ($CuCl_2 \cdot 2H_2O$) and about 258 grams potassium chloride (KCl). The resultant slurry, having a mud-like consistency, was dried at 160° C. for about 48 hours in a forced draft oven. The dried cake was broken up and ground to −70+200 mesh. The catalyst thus prepared contained about 7.9 weight percent copper, 4.0 weight percent potassium, and 9.0 weight percent chloride; had a BET surface area of about 37 square meters per gram; and had a bulk density of about 39.4 pounds per cubic foot.

EXAMPLE 2

An Inconel tube 5 feet in height and 2 inches in diameter was employed as a fluid bed oxychlorination reactor. The reactor was enclosed in a 6 inch diameter steel jacket forming an annular heat exchange system. "Dow Therm E" (a diphenyl-diphenyloxide eutectic sold by The Dow Chemical Co.) was circulated in the annular space formed between the jacket and the outer surface of the reactor to control the fluid bed temperature.

A 1 liter capacity glass secondary reactor was connected to the oxychlorination reactor vent with a glass crossover. Both the secondary reactor and the crossover were wrapped with insulation and externally controlled heating tape. The outlet of the secondary reactor was connected to a condenser system.

The oxychlorination reactor was charged to a depth of 25 inches with the catalyst prepared in Example 1 and the secondary reactor was charged with alumina. Two types of commercially available alumina were tested, i.e., Alcoa F-1 grade alumina screened to +40 mesh having a BET surface area of 300 $m^2/g$ (Type A) and Norton Co. No. SA-3232 ¼ inch alumina spheres having a surface area of 30 $m^2/g$ (Type N).

A gaseous mixture of ethylene, hydrogen chloride, and oxygen in a molar ratio of ethylene:hydrogen chloride:oxygen of 1.0:1.5:0.45 was fed to the bottom of the oxychlorination reactor and up through the catalyst bed at a rate sufficient to maintain the same in a fluidized condition. Reaction temperature was controlled at 295° C. and contact time of the gaseous reaction mixture with the fluidized catalyst was about 10 seconds.

The product gas stream from the oxychlorination reactor was fed downwardly through the alumina bed in the secondary reactor and the effluent gas from the secondary reactor was condensed and the organic and aqueous phases were submitted for analysis.

A series of runs were made using various volume ratios of Types A and N alumina to oxychlorination catalyst and at various secondary reactor temperatures and compared with a control run wherein the oxychlorination product gas stream was not passed through the alumina bed. In all of the runs, the ethylene dichloride content of the crude organic phase averaged about 97.72 weight percent with a range of from 96.63 to 98.53 percent by weight. The results and conditions of these runs are summarized in Table I.

TABLE I

Use of Secondary Alumina Reactor to Remove Chloral From Oxychlorination Product Gas Stream

| Run No. | Volume Ratio $Al_2O_3$/ OHC Catalyst | Temp. °C. | Weight % Chloral in Organic Phase | Weight % Chloral in Aqueous Phase |
|---|---|---|---|---|
| Control | — | — | 0.22 | 2.32 |
| A-1 | 0.62 | 298 | 0.02 | <0.01 |
| A-2 | 0.62 | 285 | 0.01 | <0.01 |
| A-3 | 0.62 | 160 | 0.07 | 1.50 |
| A-4 | 0.62 | 200 | 0.06 | 0.93 |
| A-5 | 0.62 | 255 | 0.01 | 0.01 |
| A-6 | 0.31 | 160 | 0.02 | 1.33 |
| A-7 | 0.31 | 200 | 0.01 | 0.11 |
| A-8 | 0.31 | 255 | 0.01 | <0.01 |
| A-9 | 0.12 | 197 | <0.01 | <0.01 |
| A-10 | 0.12 | 250 | <0.01 | <0.01 |
| A-11 | 0.12 | 298 | <0.01 | <0.01 |
| N-1 | 0.62 | 171 | 0.03 | 0.14 |
| N-2 | 0.62 | 206 | 0.06 | 0.92 |
| N-3 | 0.62 | 257 | 0.01 | 0.20 |
| N-4 | 0.62 | 295 | 0.01 | 0.07 |
| N-5 | 0.31 | 202 | 0.18 | 0.23 |
| N-6 | 0.31 | 245 | 0.04 | 0.21 |
| N-7 | 0.31 | 294 | 0.01 | 0.16 |
| N-8 | 0.12 | 185 | 0.16 | 1.33 |
| N-9 | 0.12 | 240 | 0.09 | 1.09 |
| N-10 | 0.12 | 295 | 0.04 | 0.96 |
| N-11 | 0.12 | 186 | 0.14 | 1.41 |

Although the invention has been described with specific references and specific details of embodiments thereof, it is to be understood that it is not intended to be so limited since changes and alterations therein may be made by those skilled in the art which are within the full intended scope of this invention as defined by the appended claims.

I claim:

1. In a process of preparing ethylene dichloride by vapor phase oxychlorination of ethylene wherein a gaseous mixture of ethylene, hydrogen chloride, and oxygen are contacted at an elevated temperature with an oxychlorination catalyst to produce a chloral containing gaseous reaction product stream, condensing said stream and recovering ethylene dichloride from the condensation product, the improvement comprising reducing the chloral content of said gaseous reaction product stream by contacting the chloral containing gaseous reaction product stream with alumina prior to condensation of said stream.

2. The improvement of claim 1 wherein contact between the chloral containing gaseous reaction product stream and the alumina is effected by passing said stream through a fixed bed of alumina at a temperature of from about 200° C. to 300° C., said alumina having a BET surface area of from about 30 to about 600 square meters per gram, the volume of said alumina bed being from about 10 to 60 percent of the volume of oxychlorination catalyst.

3. The improvement of claim 2 wherein the chloral containing gaseous reaction product stream is contacted with the alumina bed at a temperature of from about 240° C. to about 260° C.

4. The improvement of claim 2 wherein the alumina has a BET surface area of from about 100 to about 300 square meters per gram.

5. The improvement of claim 2 wherein the volume of the alumina bed is from about 10 percent to 30 percent of the volume of oxychlorination catalyst.

* * * * *